(12) United States Patent
Krueger et al.

(10) Patent No.: US 8,423,119 B2
(45) Date of Patent: Apr. 16, 2013

(54) MARKER TRACKING AND ACCURACY VERIFICATION FOR INTERVENTIONAL MAGNETIC RESONANCE BY MEASURING MAGNETIC FIELD INHOMOGENEITY AND DETERMINING A NOISE FIGURE OF MERIT

(75) Inventors: Sascha Krueger, Hamburg (DE); Tobias Schaeffter, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1133 days.

(21) Appl. No.: 12/089,716

(22) PCT Filed: Sep. 15, 2006

(86) PCT No.: PCT/IB2006/053311
§ 371 (c)(1),
(2), (4) Date: Apr. 10, 2008

(87) PCT Pub. No.: WO2007/046011
PCT Pub. Date: Apr. 26, 2007

(65) Prior Publication Data
US 2008/0228064 A1    Sep. 18, 2008

Related U.S. Application Data

(60) Provisional application No. 60/727,540, filed on Oct. 17, 2005.

(51) Int. Cl.
*A61B 5/055* (2006.01)

(52) U.S. Cl.
USPC ............................................. 600/414

(58) Field of Classification Search ............ 600/414, 600/424, 411
See application file for complete search history.

(56) References Cited

U.S. PATENT DOCUMENTS

| 5,155,435 | A |   | 10/1992 | Kaufman et al. |         |
|-----------|---|---|---------|----------------|---------|
| 5,318,025 | A | * | 6/1994  | Dumoulin et al.| 600/417 |
| 5,644,234 | A |   | 7/1997  | Rasche et al.  |         |
| 5,947,900 | A | * | 9/1999  | Derbyshire et al.| 600/410 |
| 6,026,315 | A | * | 2/2000  | Lenz et al.    | 600/414 |
| 6,511,426 | B1| * | 1/2003  | Hossack et al. | 600/437 |
| 6,512,941 | B1|   | 1/2003  | Weiss et al.   |         |
| 6,813,512 | B2|   | 11/2004 | Aldefeld et al.|         |
| 7,078,901 | B2| * | 7/2006  | Feiweier et al.| 324/318 |
| 2010/0168553 | A1 | * | 7/2010 | Martel et al. | 600/411 |

FOREIGN PATENT DOCUMENTS

| JP | 2004229865 |    | 9/2004  |
|----|------------|----|---------|
| WO | 9836684    | A1 | 8/1998  |
| WO | 0175465    | A1 | 10/2001 |
| WO | 0176453    | A2 | 10/2001 |

* cited by examiner

*Primary Examiner* — Jacqueline Cheng

(57) ABSTRACT

A fiducial marker assembly (30) is tracked using a magnetic resonance scanner (10). At the tracked position of the fiducial marker assembly, local B0 magnetic field inhomogeneity is measured. A warning is issued if the measured local B0 magnetic field inhomogeneity satisfies a warning criterion. A noise figure of merit of the tracking is also determined, and the warning is also issued if the noise figure of merit satisfies a noise-based warning criterion.

16 Claims, 3 Drawing Sheets

Figure 1:
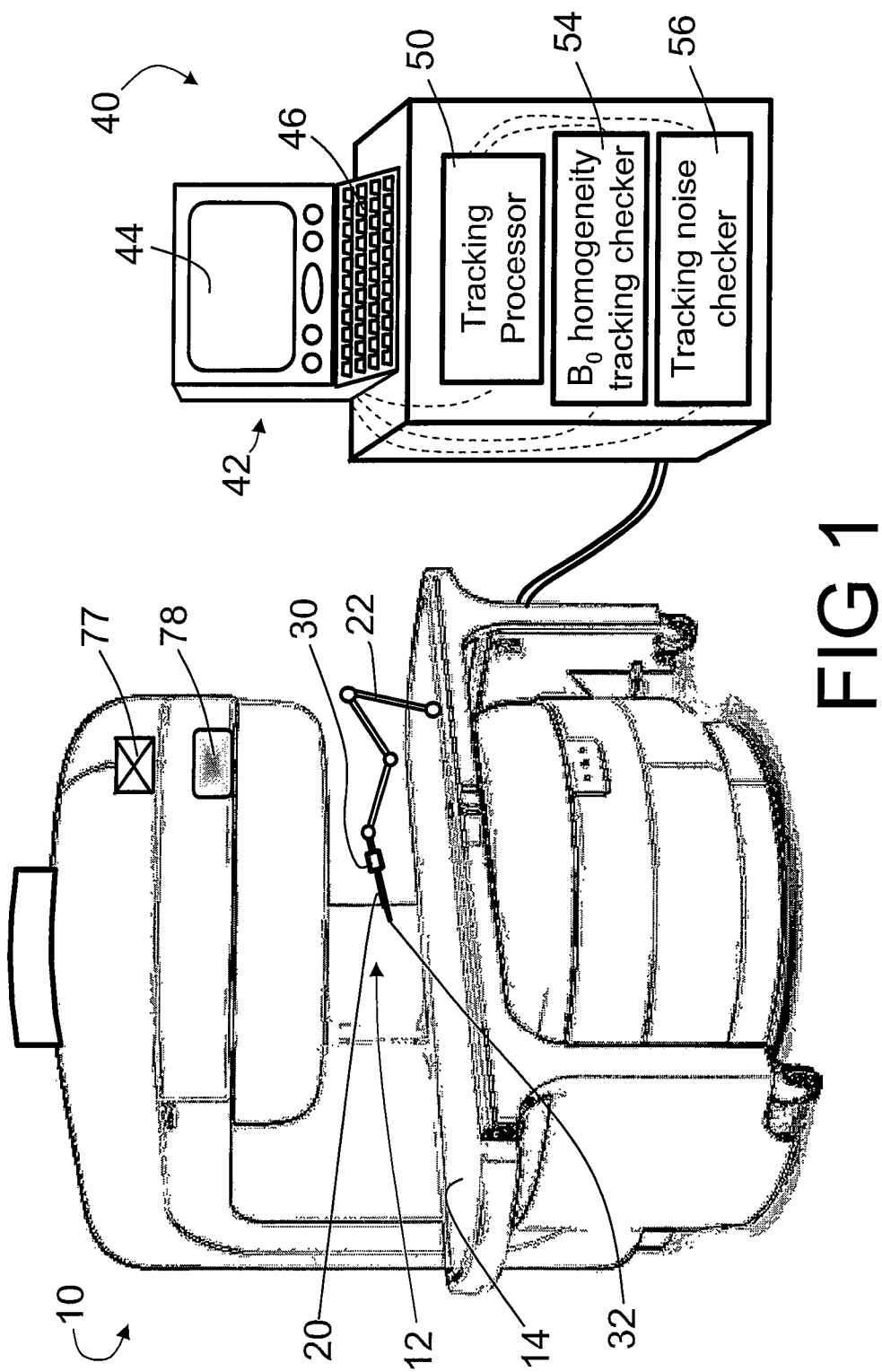

MARKER TRACKING AND ACCURACY VERIFICATION FOR INTERVENTIONAL MAGNETIC RESONANCE BY MEASURING MAGNETIC FIELD INHOMOGENEITY AND DETERMINING A NOISE FIGURE OF MERIT

CROSS REFERENCE TO RELATED APPLICATIONS

This application claims the benefit of U.S. provisional application Ser. No. 60/727,540 filed Oct. 17, 2005, which is incorporated herein by reference.

The following relates to the magnetic resonance arts. It finds particular application in locating or tracking catheters, biopsy probes, and other interventional instruments used in procedures employing interventional magnetic resonance imaging, and will be described with particular reference thereto. It finds application more generally in conjunction with locating micro-coils in the magnetic resonance scanner volume.

Interventional magnetic resonance imaging is used to guide interventional devices for procuring biopsies, locating radiation sources for brachytherapy, for targeted delivery of drugs or gene therapy, or so forth. In procedures employing interventional magnetic resonance imaging, a fiducial marker or fiducial marker assembly is disposed on or in a catheter, biopsy probe, or other interventional instrument. The fiducial marker can include an active micro-coil designed to be detected by the magnetic resonance scanner, or a passive coil or other passive marker having a magnetic susceptibility that shows up in magnetic resonance images.

A single fiducial marker arranged at the operative tip of the interventional instrument provides tip location but does not typically provide information on the orientation of the interventional instrument. Moreover, a fiducial marker positioned at the instrument tip can distort or otherwise interfere with imaging precisely at the point of intervention. Accordingly, a fiducial marker assembly including two or more (usually three or more) fiducial markers is disposed on the instrument at a defined distance from the instrument tip. By locating the markers, the location and orientation of the fiducial marker assembly is determined. As the interventional instrument has fixed orientation and position respective to the fiducial marker assembly, this in turn determines the location, and optionally the orientation, of the instrument tip.

Using such a fiducial marker assembly is complicated by the positioning of the fiducial marker assembly a distance away from the isocenter of the magnetic resonance system. In some cases, the fiducial marker assembly may be located near an edge of the field of view, for example 200 millimeters or more away from the isocenter. At these distances, the tracking accuracy decreases due to $B_0/B_1$ inhomogeneity, inadequately corrected gradient non-linearities, and so forth. If the fiducial marker assembly moves outside of the field of view, gradient ambiguity can lead to wholly erroneous tracking information. The potential for moving entirely outside of the field of view is greatest in the z-direction, since there is no inherent limit on movement through the bore.

Medical personnel rely upon tracking of the interventional instrument provided by the fiducial marker assembly during the performing of interventional procedures. If the tracking accuracy is questionable, medical personnel should be alerted. However, existing tracking systems do not provide reliable mechanisms for detecting tracking inaccuracies, or for alerting medical personnel of such tracking inaccuracies.

In one approach for ascertaining tracking accuracy, the tracking history is used to determine if and when the fiducial marker assembly leaves the field of view or other reliable tracking range. However, this approach can be compromised by low or variable tracking frame rates, and is not usable for single-shot tracking techniques.

The following contemplates improvements that overcome the aforementioned limitations and others.

According to one aspect, a tracking method is disclosed. Local $B_0$ magnetic field inhomogeneity of a $B_0$ magnetic field generated by a magnetic resonance scanner is measured at an apparent location of a fiducial marker assembly. A warning is issued if the measured local $B_0$ magnetic field inhomogeneity satisfies a warning criterion.

According to another aspect, a tracking system is disclosed. A $B_0$ homogeneity tracking checker measures local $B_0$ magnetic field inhomogeneity of a $B_0$ magnetic field generated by a magnetic resonance scanner at an apparent location of a fiducial marker assembly. A user interface issues a warning if the local $B_0$ magnetic field inhomogeneity measured by the $B_0$ homogeneity tracking checker satisfies a warning criterion.

According to another aspect, an interventional magnetic resonance system is disclosed, including a magnetic resonance scanner, a fiducial marker assembly, a tracking processor that performs tracking processing to track at least an apparent location of the fiducial marker assembly using the magnetic resonance scanner, and the $B_0$ homogeneity tracking checker and user interface as set forth in the preceding paragraph.

One advantage resides in more reliable interventional magnetic resonance tracking.

Another advantage resides in reduced likelihood of medical mistakes caused by inaccurate tracking.

Another advantage resides in providing information to medical personnel in a straightforward format as to the accuracy of tracking.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

FIG. 1 diagrammatically shows an interventional magnetic resonance system including monitoring of tracking accuracy.

Figure 2:
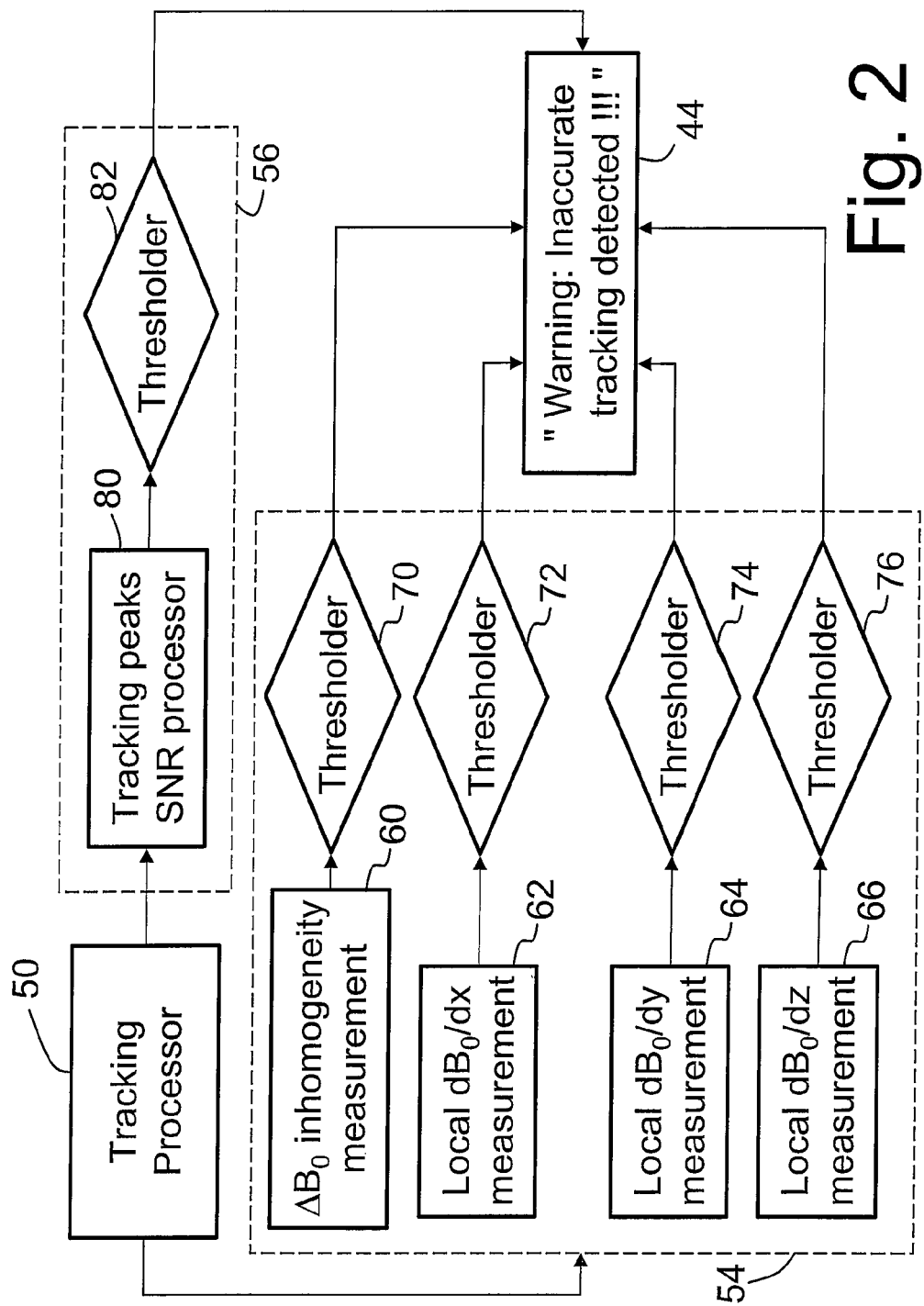

FIG. 2 diagrammatically shows electronics for tracking including monitoring tracking accuracy based on SNR and $B_0$ magnetic field homogeneity.

Figure 3:
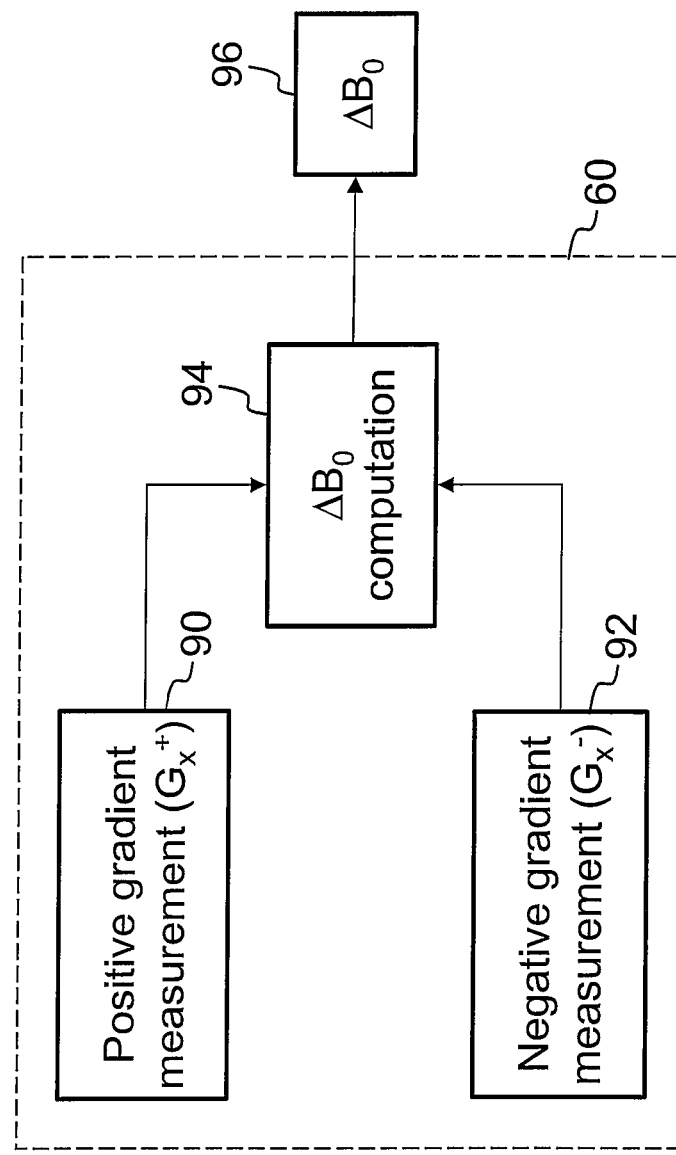

FIG. 3 diagrammatically shows a suitable processor for measuring a local $dB_0/dx$ magnetic field inhomogeneity.

With reference to FIG. 1, a magnetic resonance imaging scanner 10 performs magnetic resonance imaging in a region of interest 12. In the illustrated embodiment, the magnetic resonance imaging scanner 10 is a Philips Panorama 0.23T scanner available from Philips Medical Systems Nederland B.V. This scanner has an open bore that facilitates interventional medical procedures. It will be appreciated that the scanner 10 is an example only, and that the instrument tracking methods and apparatuses including monitoring of tracking accuracy described herein are generally applicable in conjunction with substantially any type of magnetic resonance imaging scanner, including but not limited to open bore scanners, closed-bore scanners, vertical bore scanners, and so forth. An imaging subject (not shown), such as a human medical patient, is placed on a subject support 14 and positioned within the region of interest 12 of the scanner 10.

In an interventional medical procedure, an interventional instrument 20, such as a biopsy needle, a catheter, pointer, or the like, is employed to perform a biopsy, a thermal ablation treatment, brachytherapy, slice selection, targeted drug delivery, or so forth. The magnetic resonance imaging scanner 10 images the area of the procedure during the interventional medical procedure to provide visual guidance to the surgeon or other medical therapist. In some interventional procedures, an unconstrained interventional instrument is manipulated directly by the surgeon or other medical therapist. However, for delicate or sensitive procedures which call for highly precise manipulation of the interventional instrument 20, a mechanical instrument manipulator 22 supports and manipulates the interventional instrument 20, or aids in the positioning of the interventional instrument 20, under the direction of the surgeon or other medical therapist. In the illustrated embodiment, the mechanical instrument manipulator 22 is a multi-jointed mechanical assembly providing multiple degrees of freedom for manipulating the interventional instrument 20, and is mounted to the subject support 14. In other contemplated embodiments the arm may be supported or mounted on the scanner 10 or on another associated structure.

In order to locate or track the instrument 20 during the interventional procedure, a fiducial marker assembly 30 is disposed on the interventional instrument 20 at a position expected to be within the field of view of the magnetic resonance imaging scanner 10 at least when the tip or other operational element of the instrument is at the target location. The fiducial assembly includes one or more fiducial markers to provide apparent location information pertaining to the interventional instrument 20. More typically, the fiducial marker assembly 30 includes three or more fiducial markers so as to provide both location and orientation information pertaining to the interventional instrument 20. Three fiducial markers at fixed positions relative to one another and relative to the interventional instrument 20, and with sufficient spatial distribution in three-dimensions, is generally sufficient to accurately determine the spatial location and orientation of the interventional instrument 20. Additional markers are optionally included to provide redundancy and improved tracking robustness.

In some embodiments, it is contemplated to employ only two fiducial markers in the fiducial marker assembly 30, which may be sufficient to provide both apparent location and orientation information if, for example, a rotational position of the interventional instrument 20 is unimportant. In the illustrated embodiment, the fiducial marker assembly 30 is spaced apart from an operational tip 32 of the interventional instrument 20. This arrangement advantageously reduces the likelihood that image distortions potentially caused by the fiducial marker assembly 30 will adversely affect imaging in the vicinity of the operational tip 32. However, in some contemplated embodiments the fiducial marker assembly may be positioned at the tip of the interventional instrument. In such embodiments, it is contemplated for the fiducial marker assembly to include only a single fiducial marker that indicates the apparent location of the tip without providing orientation information.

The fiducial marker or markers of the fiducial marker assembly 30 can take various forms. In some embodiments, active micro-coils serve as the markers. These active micro-coils are selectively energized during tracking portions of the magnetic resonance sequence so as to emit a signal that is tracked by the scanner 10. In some embodiments, passive fiducial markers are used, such as passive coils, vials of magnetic material, magnetically susceptible elements, or so forth. The passive marker has a magnetic susceptibility which causes the passive marker to be detected during the magnetic resonance imaging. It is also contemplated to employ a combination of active and passive markers in the fiducial marker assembly 30.

During the interventional procedure scanner electronics 40 control the magnetic resonance imaging scanner 10 to acquire imaging data, reconstruct the imaging data to generate reconstructed images, and display the reconstructed image, and also control the scanner 10 to perform tracking of the interventional instrument 20 via the fiducial marker assembly 30. In the illustrated embodiment, the scanner electronics 40 include a user interface computer 42 having a graphical display 44 and at least one input device such as a keyboard 46, mouse, trackball, or so forth, a tracking module 50 that performs tracking processing to track the interventional instrument 20 via the fiducial marker assembly 30, a $B_0$ magnetic field homogeneity tracking checker 54 that verifies accuracy of the tracking based on measurements of local $B_0$ magnetic field inhomogeneity, and a tracking noise checker 56 that verifies accuracy of the tracking based on signal-to-noise ratio (SNR) or another noise figure of the tracking.

In the illustrated embodiment, the user interface computer 42 includes hardware and/or software components (not illustrated) for controlling the scanner to acquire magnetic resonance data, to generate reconstructed images from spatially encoded magnetic resonance data, and to generate graphical renditions of the reconstructed images that are displayed on the graphical display 44. It is to be appreciated that the illustrated scanner electronics 40 are an example; in other embodiments, the tracking and/or tracking monitoring may be integrated into the computer as hardware and/or software components, or conversely data acquisition, reconstruction, and/or image rendering functionality may be embodied as electronics distinct from the computer. In some contemplated embodiments, the scanner electronics do not include a computer; rather, all data acquisition, reconstruction, image rendering, and tracking functions are performed by electronics distinct from a computer.

The tracking processor 50 employs substantially any suitable tracking technique. In some embodiments, the tracking processor 50 employs a single-shot tracking method in which a tracked position and orientation of the interventional instrument 20 is indicated responsive to medical personnel initiating a tracking frame. In some embodiments, the tracking processor 50 employs a low frame-rate iterative tracking method in which the tracked position and orientation of the interventional instrument 20 is updated automatically at a low update rate. In some embodiments, the tracking processor 50 employs a higher frame-rate iterative tracking method in which the tracked position and orientation of the interventional instrument 20 is updated automatically at a higher update rate. In some embodiments, the tracking processor 50 employs a variable frame-rate iterative tracking method in which the tracked position and orientation of the interventional instrument 20 is updated automatically at a variable update rate that depends for example, upon the last tracked position of the fiducial marker assembly 30, or upon the portion of the interventional procedure presently being performed, or so forth.

The tracking processor 50 provides apparent location information, and optionally also apparent orientation information, for the fiducial marker assembly 30 and hence also for the interventional instrument 20. The modifier "apparent" recognizes that the tracking performed by the tracking processor 50 may be less accurate than desired due to magnetic field inhomogeneity, inadequately corrected gradient non-linearities, and so forth. The $B_0$ magnetic field homogeneity tracking checker 54 verifies tracking accuracy based on measurements of local $B_0$ magnetic field inhomogeneity, and the tracking noise checker 56 verifies tracking accuracy based on SNR or another noise figure of the tracking. The $B_0$ magnetic field homogeneity tracking checker 54 provides an indication of inaccuracy in the tracking due to magnetic field inhomogeneity, inadequately corrected gradient non-linearities, and so forth. On the other hand, if the fiducial marker assembly 30 moves outside of the field of view, gradient ambiguity can lead to wholly erroneous tracking information in which the apparent location indicated by the tracking processor 50 is wholly different from the actual physical location of the interventional instrument 20. This erroneous tracking condition is detected by the tracking noise checker 56.

With continuing reference to FIG. 1 and with further reference to FIG. 2, the $B_0$ magnetic field homogeneity tracking checker 54 suitably determines a measurement 60 of the modulus of the local $B_0$ magnetic field inhomogeneity ($\Delta B_0$). Additionally a local $dB_0/dx$ measurement 62, a local $dB_0/dy$ measurement 64, and a local $dB_0/dz$ measurement 66 or other spatial derivatives or combinations of spatial derivatives are optionally determined if multiple micro-cols are available. More generally, $B_0$ magnetic field inhomogeneity derivatives are suitably measured along three mutually non-parallel directions. The local $B_0$ magnetic field homogeneity measurements are local to the tracked location of the fiducial marker assembly 30. In the illustrated embodiment, thresholders 70, 72, 74, 76 compare the measured $\Delta B_0$ inhomogeneity 60, the measured $dB_0/dx$ derivative 62, the measured $dB_0/dy$ derivative 64, and the measured $dB_0/dz$ derivative 66, respectively, with suitable warning threshold values. If any of the measured $\Delta B_0$ inhomogeneity 60, $dB_0/dx$ derivative 62, the measured $dB_0/dy$ derivative 64, or the measured $dB_0/dz$ derivative 66 exceed the warning threshold, then a warning is issued, for example by displaying text such as "Warning: Inaccurate tracking detected!!!" on the display 44 of the user interface computer 42. With brief reference back to FIG. 1, in some embodiments the user interface for issuing the warning includes an audible alarm 77, a flashing light 78 mounted on the scanner 10, or other warning indicator or combination of warning indicators that is likely to be perceived by medical personnel performing the interventional procedure.

The tracking noise checker 56 includes a tracking peaks SNR processor 80 that determines a signal-to-noise ratio of the tracking peaks. A thresholder 82 compares the determined SNR with a noise threshold value. If the SNR is less than the noise threshold value (smaller SNR implies more noise relative to the signal) then the warning of inaccurate tracking is issued. More generally, the tracking noise checker 56 determines a noise figure of merit of the tracking, and a warning is issued if the noise figure of merit satisfies a warning criterion.

With reference to FIG. 3, a suitable embodiment of the local $\Delta B_0$ measurement 60 is described. In a positive gradient measurement 90, a magnetic resonance signal is acquired for a positive applied magnetic field gradient ($G_x^+$) in e.g. the x-direction. In a negative gradient measurement 92, a magnetic resonance signal is acquired for a negative applied magnetic field gradient ($G_x^-$) in the x-direction. A suitable value of $\Delta B_0$ estimated from the two measurements 90, 92 with opposite magnetic field gradients is given by a computation 94:

$$\Delta B_0 = G_x^+ \cdot \frac{x^+ - x^-}{2}, \qquad (1)$$

where $x^+$ is the apparent position computed from the magnetic resonance signal 90 measured with the positive applied magnetic field gradient ($G_x^+$) in the x-direction, and $x^-$ is the apparent position computed from the magnetic resonance signal 92 measured with the negative applied magnetic field gradient ($G_x^-$) in the x-direction. The computation 94 of Equation (1) outputs an estimated $\Delta B_0$ value 96 that is input to the thresholder 70 of FIG. 2. Optionally, the value of $\Delta B_0$ can be analogously estimated using gradients in the y- and/or z-direction. Such measurements are typically done to determine the three-dimensional position of the micro-coil array, and can be used to increase the accuracy of the $\Delta B_0$ estimate, for example by averaging the values of $\Delta B_0$ estimated using gradients in the x-, y-, and z-directions. The local $dB_0/dx$ 62, $dB_0/dy$ 64 and local $dB_0/dz$ measurement 66 can be derived by applying the computation 94 for multiple markers (for example, four or more markers in a suitable configuration, such as along three pairwise perpendicular lines in space) and using numerical differentiation. Instead of or in addition to measuring the x, y, and z magnetic field inhomogeneity derivatives, other non-parallel magnetic field inhomogeneity derivatives can be measured. In some embodiments, only one magnetic field inhomogeneity derivative, such as the inhomogeneity derivative in the axial or z-direction parallel to the patient, is measured.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A tracking method comprising:
   tracking a fiducial marker assembly by determining an apparent location of the fiducial marker assembly using a magnetic resonance scanner;
   verifying accuracy of the tracking by measuring local $B_0$ magnetic field inhomogeneity of a B0 magnetic field generated by the magnetic resonance scanner at the apparent location of the fiducial marker assembly and issuing a warning when the measured local B0 magnetic field inhomogeneity at the apparent location of the fiducial marker assembly satisfies an inhomogeneity-based warning criterion; and
   monitoring whether the fiducial marker assembly remains in a field of view of the magnetic resonance scanner by computing a noise figure of merit of the determining of the apparent location and issuing a warning when the noise figure of merit satisfies a noise-based warning criterion.

2. The tracking method as set forth in claim 1, further including:
   locating an operational tip of an interventional instrument based on the apparent location of the fiducial marker assembly, said fiducial marker assembly including one or more fiducial markers connected with the interventional instrument.

3. The tracking method as set forth in claim 1, wherein the fiducial marker assembly includes a plurality of fiducial markers, and the tracking method further includes:

determining an apparent orientation of the fiducial marker assembly using the magnetic resonance scanner;

repeating the determining of the apparent location and the apparent orientation to track the fiducial marker assembly; and tracking an interventional instrument connected with the fiducial marker assembly based on the tracking of the fiducial marker assembly.

4. The tracking method as set forth in claim 3, wherein the plurality of fiducial markers of the fiducial marker assembly includes at least three active micro-coil fiducial markers.

5. The tracking method as set forth in claim 1, wherein the computing of a noise figure of merit comprises computing a signal-to-noise ratio (SNR) of magnetic resonance signals received during the determining of the apparent location.

6. The tracking method as set forth in claim 1, wherein the inhomogeneity-based warning criterion is satisfied when
the measured local $B^0$ magnetic field inhomogeneity is greater than a warning threshold value.

7. The tracking method as set forth in claim 1, wherein the measuring of the local $B_0$ magnetic field inhomogeneity includes:

measuring magnetic resonance signals for magnetic field gradients of opposite sign; and determining the local $B_0$ magnetic field inhomogeneity based on the measured magnetic resonance signals for applied magnetic field gradients of opposite sign.

8. The tracking method as set forth in claim 7, wherein the determining of the local $B_0$ magnetic field inhomogeneity based on the measured magnetic resonance signals for the magnetic field gradients of opposite sign includes:

computing a difference between measured apparent positions obtained from magnetic resonance signals for the magnetic field gradients of opposite sign and deriving the local $\Delta B_0$ from the computed difference.

9. The tracking method as set forth in claim 1, wherein the measuring of the local $B_0$ magnetic field inhomogeneity includes:

determining local $B_0$ magnetic field inhomogeneity components in three mutually non-parallel directions based on magnetic resonance signals measured for applied magnetic field gradients of opposite sign along each of the three mutually non-parallel directions.

10. The tracking method as set forth in claim 9, wherein the inhomogeneity-based warning criterion is satisfied when
any of the three determined local $B_0$ magnetic field inhomogeneity components exceeds a warning threshold value.

11. A tracking system comprising:

a magnetic resonance scanner configured to:

(i) perform tracking processing to track an apparent location of a fiducial marker assembly using the magnetic resonance scanner, (ii) measure local $B_0$ magnetic field inhomogeneity of a $B_0$ magnetic field generated by the magnetic resonance scanner at the apparent location of the fiducial marker assembly, (iii) measure a noise figure of merit of the performed tracking, (iv) determine tracking accuracy based on the measured local $B_0$ magnetic field inhomogeneity, and (v) determine whether the fiducial marker assembly has moved outside of a field of view of the magnetic resonance scanner based on the measured noise figure of merit; and a user interface configured to issue a warning when the determining operation (iv) satisfies an inhomogeneity-based warning criterion or the determining operation (v) satisfies a noise-based warning criterion.

12. The tracking system as set forth in claim 11, wherein the determining operation (v) includes:

determining a signal to noise ratio (SNR) of magnetic resonance peaks measured during the tracking; and thresholding the determined SNR to determine whether the SNR satisfies the noise-based warning criterion.

13. The tracking system as set forth in claim 11, wherein the determining operation (iv) includes:

thresholding the measured local $B_0$ magnetic-field inhomogeneity to determine whether the measured local $B_0$ magnetic-field inhomogeneity satisfies the inhomogeneity-based warning criterion.

14. An interventional magnetic resonance system comprising:

a magnetic resonance scanner;

a fiducial marker assembly;

a tracking system as set forth in claim 11 configured to track the fiducial marker assembly using the magnetic resonance scanner.

15. The interventional magnetic resonance system as set forth in claim 14, further including:

an interventional instrument connected with the fiducial marker assembly, the tracking system configured to track a location and orientation of the interventional instrument based on the tracking of the connected fiducial marker assembly.

16. A tracking method comprising:

tracking an apparent location of a fiducial marker assembly using a magnetic resonance scanner;

verifying accuracy of the tracking based on measured local $B_0$ magnetic field inhomogeneity of a $B_0$ magnetic field generated by the magnetic resonance scanner at the apparent location of the fiducial marker assembly; and detecting the fiducial marker assembly has moved outside of a field of view of the magnetic resonance scanner based on a measured noise figure of merit for magnetic resonance signals received during the tracking;

wherein the tracking, verifying, and detecting are performed by scanner electronics of the magnetic resonance scanner.

* * * * *